United States Patent [19]
Hodgins et al.

[11] Patent Number: 5,337,619
[45] Date of Patent: Aug. 16, 1994

[54] RADIANT ENERGY SAMPLE HEATING AND TEMPERATURE CONTROL

[75] Inventors: Bruce J. Hodgins, College Station; Robert L. Roth, Bryan, both of Tex.

[73] Assignee: O.I. Corporation, College Station, Tex.

[21] Appl. No.: 847,379

[22] Filed: Mar. 6, 1992

[51] Int. Cl.$^5$ .................. G05D 23/00; G01N 25/14; G01N 30/12; G01N 30/54

[52] U.S. Cl. ................. 73/863.11; 392/460; 392/483

[58] Field of Search ............. 73/863.11; 392/483, 392/482, 460

[56] References Cited

U.S. PATENT DOCUMENTS

| | | | |
|---|---|---|---|
| 1,505,828 | 8/1924 | Walberg | 392/482 |
| 1,814,319 | 7/1931 | Linville | 392/483 |
| 1,819,941 | 8/1931 | Brown | 604/114 |
| 1,926,958 | 9/1933 | Peterson | 219/38 |
| 2,357,286 | 9/1944 | Reavell | 219/45 |
| 2,607,877 | 8/1952 | Stevens | 392/460 |
| 2,753,246 | 7/1956 | Shields et al. | 73/863.11 |
| 2,978,562 | 4/1961 | Fox | 219/10.51 |
| 3,139,745 | 7/1964 | Sievers et al. | 392/483 |
| 3,147,366 | 9/1964 | Dreyfoos | 392/460 |
| 3,167,066 | 1/1965 | Hughes | 126/350 |
| 3,203,250 | 8/1965 | Coggeshall et al. | 73/863.11 |
| 3,505,172 | 4/1970 | Achener | 202/187 |
| 3,906,188 | 9/1975 | Gamell | 392/460 |
| 4,940,885 | 7/1990 | Challenger | 219/365 |
| 5,054,108 | 10/1991 | Gustin et al. | 392/492 |
| 5,178,019 | 1/1993 | Keiter | 73/863.11 |

FOREIGN PATENT DOCUMENTS

| | | | |
|---|---|---|---|
| 0084881 | 8/1983 | European Pat. Off. | 392/483 |
| 3243826 | 5/1984 | Fed. Rep. of Germany | 392/483 |
| 0164139 | 7/1986 | Japan | 73/863.11 |
| 4037692 | 2/1992 | Japan | 73/863.11 |

*Primary Examiner*—Hezron E. Williams
*Assistant Examiner*—George M. Dombroske
*Attorney, Agent, or Firm*—Arnold, White & Durkee

[57] ABSTRACT

A radiant energy heating source for heating the sample during purge of analytes to the sorbent trap is disclosed. The radiant energy heat source may be provided with a filter to pass only certain spectra of visible light to the sample. A thermocouple is provided to monitor the temperature of the sample and provide feedback to the radiant energy heating source.

12 Claims, 1 Drawing Sheet

RADIANT ENERGY SAMPLE HEATING AND TEMPERATURE CONTROL

BACKGROUND OF THE INVENTION

1. Field of the Invention

The present invention relates generally to sample concentration for analyzing volatile organic compounds in air, water and soils. More particularly, the invention involves a method and apparatus for radiant energy sample heating and temperature control.

2. Related Art

Sample concentrators are used in purge-and-trap, headspace, and thermal desorption gas chromatography ("GC") analysis. Purge-and-trap GC technique has been used for analyzing volatile organics in water since approximately the early 1970's. In 1987 the U.S. Environmental Protection Agency ("EPA") promulgated national primary drinking water regulations for certain volatile organic chemicals ("VOCs"). The EPA also proposed maximum contamination levels for eight volatile organic chemicals. These regulations require the use of the purge-and-trap GC technique. In addition to the eight regulated volatile organic chemicals, the EPA also promulgated monitoring requirements for an additional 52 synthetic volatile organic chemicals.

The EPA has approved certain analytical methods for analyzing these 60 compounds. One of the methods is 502.2, a purge-and-trap capillary-column GC method using a photoionization detector and an electrolytic conductivity detector joined in series. A second method is method 524.2, a purge-and-trap capillary-column GC-MS method.

Purge-and-trap systems for analyzing VOCs in drinking water have been assembled from a variety of equipment typically including a purging device, trap, and desorber. These systems also are referred to as sample concentrators. The purge-and-trap system or sample concentrator interfaces to a GC capillary column, then with a photoionization detector/electrolytic conductivity detector or a mass-spectrometer. These components are interconnected via pneumatic conduits.

Highly volatile organic compounds with low water solubility are extracted (purged) from the sample matrix by bubbling an inert gas (i.e., helium or nitrogen) through a five milliliter aqueous sample. Purged sample components are trapped in a tube containing suitable sorbent materials. When purging is complete, the sorbent tube is heated and backflushed with the inert gas to desorb trapped sample components onto a capillary GC column. The column is temperature programmed to separate the method analytes which are then detected with a photoionization detector (PID) and a halogen specific detector placed in series, or with a mass spectrometer.

Tentative identifications are confirmed by analyzing standards under the same conditions used for samples, and comparing results and GC retention times. Additional confirmatory information can be gained by comparing the relative response from the two detectors. Each identified component is measured by relating the response produced for that compound to the response produced by a compound that is used as an internal standard. For absolute confirmation, the gas chromatography/mass spectrometry (GC/MS) determination according to method 524.1 or method 524.2 may be used.

As stated above, the typical purge and trap system consists of the purging device, trap, and desorber. Systems are commercially available from several sources that meet EPA specifications.

Under EPA specifications, the glass purging device must be designed to accept five to twenty-five ml. samples with a water column at least 5 cm. deep. Gaseous volumes above the sample are kept to a minimum to reduce "dead volume" effects. The purged gas passes through the water column as finely divided bubbles.

The sorbent trap is a tube typically at least 25 cm. long and having an inside diameter of at least 0.105 inches. The trap contains certain sorbent materials which the EPA has specified as 2,6-diphenylene oxide polymer, silica gel, and coconut charcoal. The EPA regulations specify the ratios of the adsorbent material. The desorber must be capable of rapidly heating the trap to 180° C.

The model 4460A sample concentrator manufactured by OI Analytical of College Station, Tex., is an example of a purge and trap, or sample concentrator, device. The model 4460A is a microprocessor controlled device that stores method 502.2 and 524.2 operating conditions as default parameters. Operating conditions may be changed by the user to accommodate other types of purge and trap analysis.

In addition to purge-and-trap methods and analyses, sample concentration gas chromatography is used in headspace analysis of liquids and solids, and in thermal desorption analysis of air tube samples. Headspace and thermal desorption techniques are not only used for environmental analyses, but also for clinical and industrial applications.

EPA standard 502.2 specifies purging 5 milliliters of water per 11 minutes. EPA standard 524.2 specifies 25 milliliters. This time period is an attempt to compromise the optimal purging time for a broad range of analytes, each having different volatility and solubility characteristics. By heating the water sample, it is possible to accelerate the volatility and decrease the solubility of analytes to more completely purge each of the analytes out of solutions during the same time period.

Sample containers, or sparge vessels, are conventionally heated by placing a heater jacket, or pocket heater, around the glass outside surface of the sparge vessel. By contacting the outside surface of the sparge vessel, the pocket heater conducts heat to the sample in the vessel. One example of such a device is the TEKMAR pocket heater, which may be placed around the outside of a sparge vessel.

Another type of heater assembly for sparge vessels is the tube type heater which fits snugly against the outside of the glassware. Pocket heaters and tube heaters are conventionally heated with electric current to the temperature of as high as 100° C.

Although the pocket heater and tube heater are advantageous in that they are inexpensive and simple to use, a problem encountered in their use is delay for transferring heat from the jacket or tube to the inside of the sparge vessel. Even if the temperature of the jacket or tube heater is precisely regulated, that same temperature may not necessarily be reached at the inside of the vessel.

The use of conductive heating of samples has other disadvantages and problems. There is a time delay in first heating the jacket (for example, 5 minutes), and then transferring the heat to the sample (for example, an additional 7 or 8 minutes).

Similarly, with these heating systems it is not possible to heat all samples uniformly. This problem is in part due to the fact that the jacket does not have a uniform fit around the sparge. Typically, a thermocouple is used to monitor the temperature of the jacket. However, even if the temperature of the jacket is known, the temperature of the sample may be significantly lower. Therefore, it may be necessary to compensate for this difference by increasing the jacket temperature.

As a result of these problems, each sample may be at a different temperature, and may be purged at a different rate. This means that interpretation of GC results and detection of analytes is less reliable and consistent from one sparge vessel to the next.

SUMMARY OF THE INVENTION

The present invention overcomes the above-mentioned disadvantages and problems by providing a method and apparatus for radiant energy sample heating and temperature control. The heating method involves a heat source that provides radiant heat energy to the sample through the transparent glass of the sparge vessel. The present invention involves the use of radiant heat rather than conductive heat. The invention also includes a thermocouple in the sparge vessel to monitor the sample temperature and provide feedback of temperature to the heating source.

DETAILED DESCRIPTION OF THE PREFERRED EMBODIMENT

Figure 1:
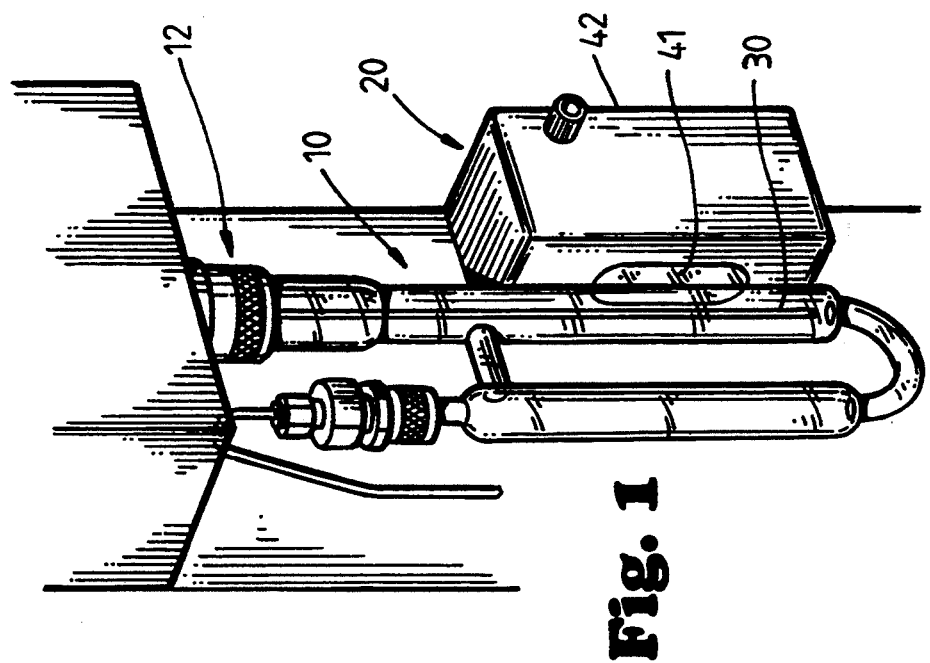
FIG. 1 is a perspective view of the radiant energy heating device according to a preferred embodiment of the invention.

As shown in FIG. 1, a sparge vessel 10 is positioned in a sample concentrator for purging of analytes from a water sample. Typically, the sparge vessel includes a concentrator inlet 12 at the open end thereof. Helium or nitrogen gas is introduced to purge the analytes from the water sample. As discussed above with respect to method 502.2, the glass sparge vessel is designed to accept five ml. samples with a water column at least five cm. deep. The purge gas passes through the water as finely divided bubbles.

Figure 2:
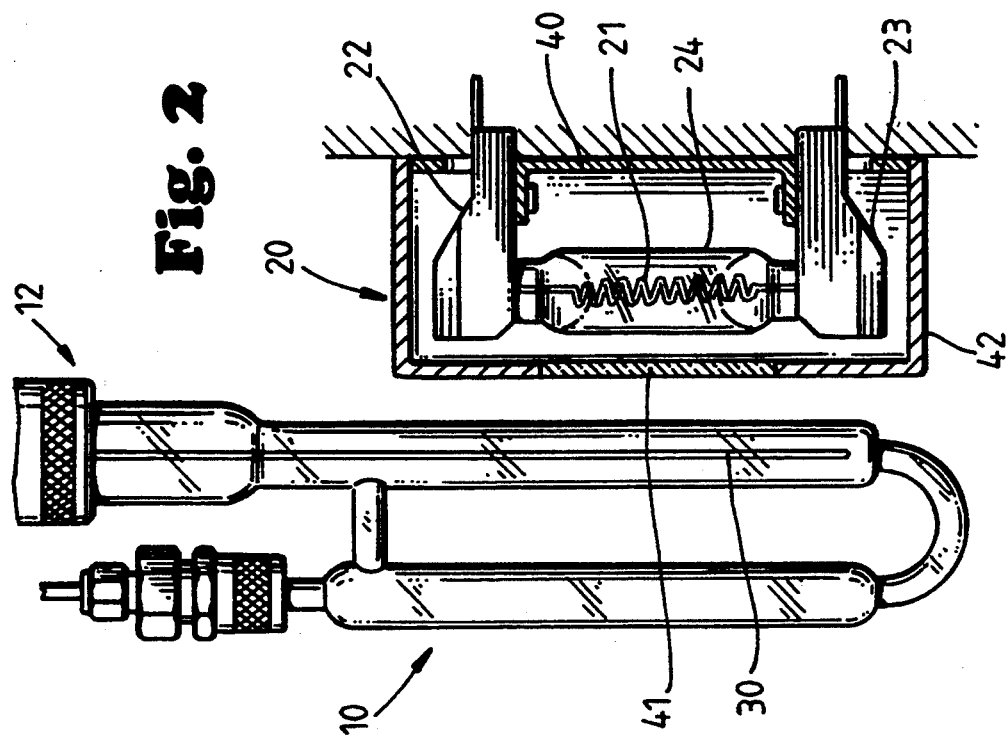
FIG. 2 is a side view, partial in section, of a preferred embodiment, of the present invention.

As shown in more detail in FIG. 2, adjacent the sparge vessel is radiant energy heat source 20 having a tungsten filament 21, which is heated by introducing electrical current to the filament by conventional means through connections 22 and 23. Other filaments may be used depending on the temperature and heat requirements. In a preferred embodiment, the radiant energy heat source is a bulb 24 having a quartz casing enclosing an inert gas, and having a power of 100 to 1000 watts. Most preferably, the power consumed is 250 watts.

Preferably, the radiant energy heat source 20 is positioned approximately one to two centimeters from the sparge vessel. The radiant energy heat source 20 is preferably positioned in a vertical alignment to reflect radiant energy along substantially the entire vertical dimension of the sparge vessel.

A thermocouple 30 provides exact temperature readout from the sample and provides feedback to the radiant energy heat source. Monitoring the temperature of each sample provides more accurate and repeatable purging of different samples than with the prior art.

This temperature monitoring also is advantageous because the radiant energy heat source can reach temperatures in excess of 1000 degrees C. which would be excessive if that heat were transferred to the sample and the sample temperature were not monitored. Specifically, it is desirable to heat the sample to somewhere between 50° C. and 85° C. This means that power to the radiant energy heat source is turned off when the sample reaches a desired temperature.

The invention further includes a reflecting surface 40 which has a concave surface to direct the light energy at the sparge vessel. Further, in a preferred embodiment a filter 41 is placed in casing 42 to position the filter between the radiant energy heat source and the sample. The filter 41 reduces the amount of visible light and passes only certain portions of the spectrum to the sample. For example, only infrared light may be passed.

When multiple sparge vessels are used in a sample concentrator, i.e., an automatic sampler, one radiant energy heat source may be used for each vessel. Or, if desired, the heat source may be configured and positioned to direct heat to more than one sparge vessel.

The present invention involves heating a sample with radiant energy rather than conductive energy. Further, the present invention provides thermocouple feedback between the sample and the heat source.

An important advantage of the present invention is that it more accurately and repeatably heats the sample to a desired temperature and therefore improves uniformity and detection for the GC.

Another advantage is that it more rapidly heats the sample from ambient to the desired temperature. For example, the present invention is capable of heating the sample from ambient to 50 degrees C. in approximately 30 seconds Although variations in the embodiment of the present invention may not each realize all the advantages of the invention, certain features may become more important than others in various applications of the device. The invention, accordingly, should be understood to be limited only by the scope of the appended claims.

What is claimed is:

1. A system for heating a water sample comprising:
    a. a sparge vessel at least five centimeters deep for holding the water sample in a column;
    b. a radiant energy heat source spaced from the sparge vessel;
    c. thermocouple means functionally connected between the water sample in the column and the radiant energy heat source; and
    d. switch means for turning off the radiant energy heat source when the water sample reaches a desired temperature between 50 degrees C. and 85 degrees C.

2. The system of claim 1 further comprising a filter for passing only infrared light from the radiant energy heat source to the water sample.

3. The system of claim 1 wherein the radiant energy heat source is a tungsten filament.

4. A system for purging volatile organic chemicals from a water column, comprising:
    (a) a glass sparge vessel at least five centimeters in depth for holding the water column;
    (b) an electric light source positioned adjacent the water column, the light source being at a temperature greater than 100 degrees C.;
    (c) means for automatically turning on and off the electric light source to maintain the water column at a selected temperature below 100 degrees C.; and (d) means for bubbling an inert gas through the water column.

5. The system of claim 4, further comprising a reflecting surface positioned adjacent the electric light source to direct the light towards the water column.

6. The system of claim 4, further comprising a filter positioned between the electric light source and the water column to pass only selected portions of the light spectrum to the water column.

7. The system of claim 4, wherein the electric light source is positioned to emit light rays to cover substantially the entire surface of the water column which is in closest proximity to the electric light sources.

8. The system of claim 4, wherein the water column is heated to a selected temperature of between 50 degrees C. and 85 degrees C.

9. A system for purging analytes from a liquid, comprising:

(a) a glass sparge vessel at lest five centimeters deep for holding the liquid in a column;

(b) a light-generating source positioned between one and two centimeters from the sparge vessel, the light-generating source configured to reach a temperature above the boiling point of the liquid in the sparge vessel;

(c) light reflecting means positioned adjacent the light-generating source to reflect the light onto the sparge vessel; and (d) temperature monitoring means functionally connected to the liquid in the sparge vessel to reduce the intensity of the light-generating source when the temperature of the liquid reaches a desired value below the boiling point of the liquid.

10. The system of claim 9 further comprising a filter for reducing the amount of visible light reflected onto the sparge vessel.

11. The system of claim 9 wherein the light-generating source is a tungsten filament.

12. The system of claim 9 wherein the temperature monitoring means is a thermocouple.

* * * * *